United States Patent
Pressman et al.

(12)

(10) Patent No.: US 6,197,916 B1
(45) Date of Patent: Mar. 6, 2001

(54) METHOD FOR PREPARING BISPHENOL A

(75) Inventors: Eric James Pressman, East Greenbush; Joseph Richard Wetzel, Watervliet, both of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/385,680

(22) Filed: Aug. 30, 1999

Related U.S. Application Data

(62) Division of application No. 09/144,487, filed on Aug. 31, 1998, now Pat. No. 5,990,362.

(51) Int. Cl.[7] .......................... C08G 59/62; C08G 65/38; C07C 37/68
(52) U.S. Cl. .............. 528/110; 528/86; 528/97; 528/106; 528/176; 528/185; 528/218; 528/219; 568/724
(58) Field of Search .............. 568/724; 528/219, 528/218, 67, 86, 97, 106, 110, 176, 185

(56) References Cited

U.S. PATENT DOCUMENTS

| 4,286,083 | * | 8/1981 | Kochanowski | 528/173 |
|---|---|---|---|---|
| 4,346,249 | * | 8/1982 | Krabbenhoft | 568/782 |
| 4,391,998 | * | 7/1983 | Wu . | |
| 5,243,093 | * | 9/1993 | Kissinger et al. . | |
| 5,274,068 | | 12/1993 | Boden et al. | 528/179 |
| 5,475,152 | * | 12/1995 | Kissinger et al. . | |
| 5,723,688 | * | 3/1998 | Patrascu et al. . | |
| 5,723,689 | | 3/1998 | Pressman et al. | 568/724 |

FOREIGN PATENT DOCUMENTS

| 1260478 | 2/1968 | (DE) . |
|---|---|---|
| 0153680 | 1/1982 | (DE) . |
| 945420A1 | 9/1999 | (EP) . |

OTHER PUBLICATIONS

International Search Report.

* cited by examiner

*Primary Examiner*—Floyd D. Higel
*Assistant Examiner*—Ebenezer Sackey
(74) *Attorney, Agent, or Firm*—Noreen C. Johnson; Douglas E. Stoner

(57) ABSTRACT

A method for preparing bisphenol A is disclosed, with a selectivity for the p,p'-isomer of greater than about 97%. The method involves reacting phenol with p-isopropenylphenol or 2-(4-hydroxyphenyl)-2-propanol in the presence of a catalyst, at a reaction temperature of no greater than about 65° C. The bisphenol A product is preferably purified by a technique which omits the use of adduct crystallization.

8 Claims, No Drawings

METHOD FOR PREPARING BISPHENOL A

This appln is a Div of Ser. No. 09/144,487 filed Aug. 31, 1998 now U.S. Pat. No. 5,990,362.

TECHNICAL FIELD

This invention relates generally to polyhydroxy compounds which are useful for resin synthesis. More particularly, it is directed to an improved method for preparing high-purity bisphenol A.

BACKGROUND OF THE INVENTION

Bisphenol A is a very important monomer in polymer synthesis. It is the key starting material for most epoxy materials, as well as most polycarbonates. Commercial output for bisphenol A on an annual basis exceeds 5 billion pounds.

Most often, bisphenol A is prepared by the acid-catalyzed condensation of phenol and acetone. For example, phenol (in excess) and acetone can be mixed and warmed to about 50° C. A homogeneous catalyst such as hydrogen chloride (HCl) is passed into the mixture over an extended period of time. A promoter-agent such as a thiol-based compound is frequently required to achieve commercially-acceptable reaction rates and selectivity.

The bisphenol A product (or an adduct of bisphenol A and phenol) precipitates, and can be filtered off and washed with a suitable solvent like toluene or phenol. The solvent treatment removes the unreacted phenol, which is recovered for re-use. The bisphenol A product can then be subjected to a "first-stage" purification by a variety of techniques, e.g., recrystallization or melt crystallization.

While the use of homogeneous catalysts had been favored for preparing bisphenol A for many years, the use of a heterogeneous catalyst system has become the most popular technique. Most of the heterogeneous catalysts are ion exchange resins, e.g., sulfonated polystyrene resins which utilize divinyl benzene as a cross-linking agent. The heterogeneous catalysts systems provide important advantages. For example, they are non-corrosive (in contrast to HCl); they can be readily separated from the reaction mixture; and they are very amenable to continuous reaction operation.

Regardless of the catalyst system used in the preparation of bisphenol A, the purity of the product is generally extremely important. For almost all applications, the para, para-isomer of bisphenol A (sometimes referred to herein as "p,p'-bisphenol A") is highly preferred, in contrast to the ortho,para- and ortho,ortho-isomers. Thus, for the purpose of this disclosure, the degree of "purity" generally refers to the maximum level of p,p'-bisphenol A present in the product mixture, as well as the minimum level of other impurities present, such as cyclic dimers derived from bisphenol A, chroman-based compounds, spirobiindane compounds, and the like. As used herein, "selectivity" is a more specific definition than "purity", referring to the percentage of p,p'-bisphenol A present in a reaction product mixture rendered free of phenol, acetone, and water. As noted above, it is desirable that the proportion of p,p'-bisphenol A be as high as possible.

In the case of epoxy resins, the purity of bisphenol A is not particularly critical, since color and high molecular weight are not usually important requirements. Thus, a material containing about 95–98% by weight of the p,p'-isomer might be quite sufficient. (The primary impurity for such a material would be the ortho, para isomer).

However, the bisphenol A used to prepare most polycarbonates must be of ultra-high purity, e.g., greater than about 99.5% and preferably, greater than about 99.9%. Impurities in the bisphenol A could lead to colored products, which would render the material useless for applications such as glazing. Moreover, the presence of impurities can prevent the build-up in molecular weight which is required for most polycarbonate materials.

The reaction processes currently used on a commercial scale often provide an "intermediate" product which is 70% selective to p,p'-bisphenol A. The product is then subjected to one or more purification steps which eliminate almost all impurities, and raise the selectivity to greater than about 98%. Many of the impurities are eliminated by being re-exposed to reaction conditions, which result in their isomerization to p,p'-bisphenol A. As an example, the reaction effluent is often treated in an adduct crystallizer.

Adduct crystallization processes typically involve, as a first step, the distillation (under reduced pressure) of a product mixture of bisphenol A, unreacted phenol, unreacted acetone, water, and by-products, so as to remove the water, acetone, and a small portion of the phenol. The remaining liquid mixture is cooled, resulting in the crystallization of an adduct of bisphenol A with phenol, as described in U.S. Pat. No. 5,723,688. The adduct crystals are then separated from the mother liquor, and phenol is removed from the adduct, thereby yielding the bisphenol A. After multiple passes through the adduct crystallizer, the effluent is very pure, with a selectivity at or close to the desired level. Typically, the effluent is then passed to another purification system, such as a melt crystallizer, which eliminates substantially all remaining impurities (including the o,p and o,o' isomers). The selectivity of the product which exits the melt crystallizer is usually greater than about 99.9% p,p'-bisphenol A.

The final bisphenol A product possesses the desired level of purity and selectivity. However, the purification steps required to attain that objective—such as adduct crystallization—add a great deal of expense to the overall manufacturing process. It is estimated that at least 60% of the cost of most commercial bisphenol A operations is typically related to purification of the product in the reactor effluent. In addition to capital (e.g., equipment) costs, current purification procedures require considerable periods of processing time. Moreover, since new uses for polymers made with bisphenol A require ever-increasing levels of purity for the raw materials, there is presently very little flexibility in the purification steps. Furthermore, when high-quality parameters are coupled with requirements that products be prepared at lower cost, a manufacturer is faced with a serious dilemma.

It should thus be apparent that new methods for preparing bisphenol A would be welcome in the art. In U.S. Pat. No. 4,346,249 (H. Krabbenhoft), the preparation of bisphenol A by a reaction which involves p-isopropenylphenol is briefly mentioned. However, the patent does not provide any teaching as to the preparation of bisphenol A with a high degree of purity, and with high selectivity toward the para, para-isomer of the product.

New methods for preparing bisphenol A should result in a product with high purity and selectivity. The methods should also reduce or eliminate the need for extensive purification treatments of the "raw" bisphenol A product. It would also be desirable if the new methods could be carried out by using a heterogeneous catalyst system which does not always require the use of a promoter (sometimes referred to as a "co-catalyst"). Moreover, in some instances, it would be useful if the new methods did not rely on acetone as a starting material.

SUMMARY OF THE INVENTION

The needs discussed above have been satisfied by the discovery which forms the basis for the present invention. In one embodiment, the invention is directed to a method for preparing bisphenol A, with a selectivity for the p,p'-isomer of greater than about 97%. The method comprises the step of reacting phenol with p-isopropenylphenol or 2-(4-hydroxyphenyl)-2-propanol in the presence of a catalyst, at a reaction temperature of no greater than about 65° C. In preferred embodiments, the reaction temperature is no greater than about 60° C. An ion exchange resin catalyst system is often employed, preferably in the absence of a co-catalyst, e.g., in the absence of a thiol promoter.

Moreover, in preferred embodiments, the bisphenol A product is purified by a technique which omits the use of adduct crystallization, thereby advantageously streamlining the overall manufacturing process. This important advantage occurs because, as compared to the prior art, the present process produces a much "cleaner" intermediate product prior to the purification stage.

Other embodiments of this invention call for the reagent p-isopropenylphenol to be prepared by dehydrogenating p-isopropylphenol. Furthermore, the p-isopropylphenol can be obtained by the reaction of phenol and propylene.

Still another embodiment of the invention is directed to an improved method for preparing a polycarbonate polymer, involving the reaction of bisphenol A and a carbonate precursor, wherein the bisphenol A is prepared as described below.

Further details regarding the various aspects of this invention are provided in the remainder of the disclosure.

DETAILED DESCRIPTION OF THE INVENTION

As mentioned above, the present invention calls for the reaction of p-isopropenylphenol or 2-(4-hydroxyphenyl)-2-propanol (sometimes referred to herein as the "carbinol") with phenol, in the presence of a suitable catalyst. p-Isopropenyl-phenol can be obtained from a variety of sources. For example, it can be obtained by reaction of a methyl Grignard reagent with para-hydroxyacetophenone or methyl para-hydroxybenzoate, followed by dehydration.

More often, p-isopropenylphenol is made by way of the catalytic dehydrogenation of para-isopropylphenol with various catalysts, such as a mixture of chromium oxide and aluminum oxide, or a mixture of magnesium oxide, iron oxide, copper oxide, and potassium oxide. The p-isopropylphenol itself can be obtained by various techniques, such as the reaction of phenol and propylene, or the hydroxylation of cumene.

In some preferred embodiments, a calcium-nickel-phosphate catalyst system is used to form p-isopropenylphenol. Such a catalyst is described in U.S. Pat. No. 4,346,249 (H. Krabbenhoft), which is incorporated herein by reference. As one specific example, p-isopropylphenol, phenol and water can be passed over a calcium-nickel-phosphate catalyst bed at a temperature of about 275° C. to about 500° C. Typically, 0.5 to 5 moles of phenol and 0.5 to 4 moles of water are used for each mole of p-isopropylphenol. The catalyst has usually been calcined prior to use.

The carbinol (2-(4-hydroxyphenyl)-2-propanol) can also be prepared by techniques known in the art. One method, described more fully in the examples, calls for the reaction of a methyl-containing compound like methyllithium (usually dissolved in an ether solvent) with an appropriate ester, e.g., methyl-4-hydroxybenzoate. In this manner, a methyl anion would add twice to the ester, to form the carbinol. Alternatively, the methyl-containing compound can be reacted with a methyl ketone, such as 4-hydroxy acetophenone. In that instance, the ketone simply undergoes 1,2-addition, to form the carbinol.

p-Isopropenylphenol is not a stable compound at room temperature, since it has the tendency to undergo self-alkylation. Thus, when the compound is to be used to prepare bisphenol A, it should be used relatively quickly, or stored at a temperature below its freezing point, i.e., 0° C., without significant exposure to light. On the other hand, 2-(4-hydroxyphenyl)-2-propanol is quite stable, and does not require special storage requirements. For this reason, the carbinol is sometimes preferred in making bisphenol A according to this invention.

A variety of catalyst systems may be used in the process of the present invention. Homogeneous catalysts like hydrochloric acid, sulfuric acid, or Lewis acids would be suitable for some embodiments. However, heterogeneous catalyst systems are preferred. In particular, the use of an ion exchange resin is often the most efficient means of catalysis. These resins participate in fewer side reactions. Moreover, because they are insoluble, they remain in the reactor system, do not have to be recovered, and do not contribute to downstream corrosion problems.

Ion-exchange resins are well-known in the art and described in various sources, such as Kirk-Othmer's *Encyclopedia of Chemical Technology*, 3rd Edition, Vol. 9, pp. 256 and 296–297 (1980); and Vol. 13, pp. 678 et seq. (1981). The use of ion-exchange resins for catalysis is also described in Kirk-Othmer's *Encyclopedia of Chemical Technology*, 4th Edition, Vol. 14, pp. 777–778 (1995).

Cationic exchange resin s are often the preferred type of catalysts for the present invention. In particular, strong-acid types of resins are suitably employed. Non-limiting examples include sulfonated copolymers of styrene and a cross-linking agent, e.g., a difunctional monomer like divinylbenzene. Commercial examples of suitable ion exchange resins are the Amberlyst® materials (e.g., Amberlyst® 15) and Amberlite® materials (e.g., Amberlite® 131 and Amberlite® 118), available from Rohm & Haas Company; and the Dowex® products which are available from Dow Chemical Company.

In prior art processes for preparing various bisphenols, the ion exchange resin catalysts often required pre-treatment with a sulfur-comprising promoter. Examples included thiol (mercaptan)-based compounds which were covalently or ionically linked/bonded to the catalyst. This type of material may be used in some embodiments of the present invention. However, preferred embodiments do not require the use of such a co-catalyst. The absence of the co-catalyst can represent considerable savings—especially in a larger-scale manufacturing operation.

A critical limitation for the reaction of p-isopropenylphenol or 2-(4-hydroxyphenyl)-2-propanol with phenol according to the present invention is reaction temperature. The present inventors discovered that the reaction could be successfully carried out under unusually mild conditions, i.e., a reaction temperature no greater than about 65° C. In preferred embodiments, the temperature is no greater than about 60° C., and in especially preferred embodiments, is no greater than about 50° C.

In addition to the energy savings provided by the decreased temperatures, the overall process surprisingly results in a selectivity for the p,p'-isomer of bisphenol A of greater than about 97%. More often, the selectivity is greater than about 98%. As further described below, the high selectivity obtained as a consequence of the reaction process itself results in an extremely favorable simplification of the subsequent purification processes to obtain the final bisphenol A product.

There are no special steps involved in reacting the phenol with p-isopropenylphenol or the carbinol. Both of the latter components are readily soluble in phenol, so reaction mixtures can easily be prepared. An excess of phenol is typically used in the reaction mixture. When using p-isopropenylphenol, the molar ratio of phenol to p-isopropenylphenol is at least about 4:1, and preferably, at least about 16:1. These relatively high ratios help to prevent the p-isopropenylphenol from reacting with itself, e.g., to form a linear dimer of the compound. When using 2-(4-hydroxyphenyl)-2-propanol, the molar ratio of phenol to 2-(4-hydroxyphenyl)-2-propanol is usually about 4:1 and preferably, about 16:1. The reaction may be carried out in an inert atmosphere.

In the case of ion exchange resin catalysts, the resin bed is often confined in a column, which could be a gently-stirred tank. The ion exchange resin can be formed into beads, which are sulfonated, and which can then be packed into the column. Sometimes, the beads are initially mixed with a portion of the phenol to be used in the reaction (as described in the examples). A phenolic solution which contains p-isopropenylphenol or the carbinol can then be pumped through the column to carry out the reaction. The reaction usually occurs very quickly, and conventional techniques can be used to measure the completion of the reaction, e.g., gas- or liquid chromatography.

The bisphenol A product can be recovered and purified by procedures known in the art. As an example, crystallization and/or precipitation is often used in manufacturing operations to separate and purify the desired product. A wide variety of crystallization techniques are known in the art. Some are described in *Ullmann's Encyclopedia of Industrial Chemistry*, Volume B2, VCH Publishing, 1988, which is incorporated herein by reference. Non-limiting examples include evaporating crystallizers, vacuum crystallizers, forced-circulation crystallizers, fluidized-bed crystallizers, adduct crystallizers, and melt crystallizers.

Although the final bisphenol A product must be very pure, it is highly desirable to reduce the crystallization/purification operations as much as possible (as described previously), to reduce processing time and costs. Thus, in some preferred embodiments of this invention, time-consuming and costly operations like adduct crystallization are not employed, in contrast to typical processes of the past. Instead, the "raw" bisphenol A product resulting from the reaction process disclosed herein has an inherent purity high enough to permit final purification by way of a simpler technique. In preferred embodiments of this invention, the bisphenol A product mixture which results after phenol is reacted with p-isopropenylphenol or 2-(4-hydroxyphenyl)-2-propanol (and after the volatiles like unreacted phenol and water are removed) is characterized by a selectivity for the p,p'-isomer of greater than about 97%, and preferably, greater than about 98%. Moreover, the level of non-bisphenol A byproducts is less than about 3%, and preferably, less than about 2%, based on the weight of the product mixture.

One exemplary technique which can be used as the sole means of purification for the bisphenol A product mixture is melt-crystallization. Any operation which is capable of removing impurities (i.e., the ortho,para-isomer of bisphenol A, as well as any other remaining impurities, e.g., cyclic dimers derived from bisphenol A; chromans; and the like) from a reaction melt may be employed. Various aspects of melt crystallization are described in the *Ullmann's* text mentioned earlier. As described therein, melt crystallization can occur in one stage or multiple stages. In general, melt crystallization is usually carried out by one of two basic techniques: (1) rapid crystallization of discrete crystals in the body of a vessel which is being agitated; and (2) gradual deposition of a crystalline layer on a chilled surface in a static or laminar flowing melt.

Most often, melt crystallization of a product mixture which contains bisphenol A is carried out with the use of a zone-melting or zone-refining apparatus. These techniques are briefly described in U.S. Pat. No. 5,723,689, incorporated herein by reference. Usually, they include means for freezing and melting the product mixture. The melting and freezing temperatures to which the mixture is subjected are those which allow for the substantially-pure p,p'-bisphenol A to crystallize, while impurities are collected in the resulting molten phase. An apparatus for carrying out this type of melt crystallization is described in *Modern Methods of Chemical Analysis* (1968), pages 15–16, which is incorporated herein by reference.

While melt crystallization is preferred, other techniques can sometimes be used in its place, and in the absence of adduct crystallization. Examples include solvent crystallization from toluene, water, methylene chloride, and the like. As still another alternative, the p,p'-bisphenol A could be distilled from the reaction mixture, at atmospheric or reduced pressure.

After post-reaction purification is complete (i.e., after melt crystallization), the bisphenol A product usually has a purity of at least about 99.7%, and preferably, at least about 99.9%. As noted previously in regard to the term, "purity" relates to the percentage of the para, para isomer of bisphenol A present, i.e., excluding all other isomeric forms of bisphenol A and all other non-bisphenol A compounds.

Another embodiment of this invention is directed to a process to make a polycarbonate polymer, using the bisphenol A product prepared as described previously. Details regarding the preparation of polycarbonates are well-known in the art and described, for example, in *Organic Polymer Chemistry*, by K. J. Saunders, 1973, Chapman and Hall Ltd., the relevant passages of which are given here.

Preparation

There are two main methods for the manufacture of poly(2,2-bis(4'-phenylene)propane carbonate), namely direct phosgenation and ester interchange.

Direct phosgenation

In this method, the polymer is obtained by a Schotten-Baumann reaction by treating bisphenol A directly with phosgene in the presence of base.

The simple method of passing phosgene into a solution of bisphenol A in aqueous sodium hydroxide is unsatisfactory because the growing polymer becomes insoluble in alkali and only low molecular weight material is obtained. Two techniques have been devised to circumvent this difficulty, namely the solution method and the interfacial method.

Solution Method

In this method the reaction is carried out in pyridine, which is a solvent for the reactants and polymer; the pyridine also acts as a catalyst and combines with the hydrogen chloride formed. Because of the high cost of pyridine, the process is generally carried out using a mixture of pyridine and a cheaper solvent such as chloroform, methylene chloride or 1,1,2,2-tetrachoroethane. Typically, phosgene is passed into the bisphenol A solution at 23–35° C. Pyridine hydrochloride is precipitated and a viscous solution of polymer is rapidly formed. The solution is then washed with dilute hydrochloric acid (which converts any free pyridine into the corresponding water-soluble salt) and then with water until the washings are free from ionic contaminants. Practically, effective washing of the viscous polymer solution is difficult. The polymer is then isolated either by precipitation with a non-solvent such as methanol or by evaporation. The product is finally extruded and pelletized. The pyridine and other solvents used are recovered and recycled.

Interfacial Method

In this method a solution of bisphenol A in aqueous sodium hydroxide is dispersed in an organic solvent such as methylene chloride by rapid stirring. A small quantity of tertiary amine (e.g., triethylamine) or quaternary ammonium base (e.g., tetramethylammonium hydroxide) is added to the system as catalyst and then phosgene is passed in at about 25° C. When reaction is complete the organic phase, which contains the polymer, is separated and the polymer is isolated as in the solution method described above.

Ester Interchange

In this method, the polymer is obtained by ester interchange between bisphenol A and diphenyl carbonate. In order to obtain high yields of polymer and high molecular weights, almost complete removal of phenol from the reaction mixture is required.

In a typical process, a mixture of bisphenol A and diphenyl carbonate together with a basic catalyst (e.g., lithium hydride, zinc oxide or antimony oxide) is melted and agitated at about 150° C. under nitrogen. The temperature is then raised to about 210° C. over 1 hour and the pressure is reduced to about 20 mm Hg. By the end of this time most of the phenol has been distilled off. The reaction mixture is then heated for a further period of 5–6 hours during which time the temperature is raised to about 300° C. and the pressure is lowered to about 1 mm Hg. During this period the melt becomes increasingly viscous and the reaction is eventually stopped while the material can still be forced from the reactor under inert gas pressure. The extruded material is then pelletized.

The polymer is processed mainly by injection moulding and the electrical and the electronics industries are the largest users; moldings are used for battery parts, coil formers, fuse covers and a host of other components. There is also some use in domestic mouldings such as food mixer housings, kitchen utensils and babies' bottles. Both interfacial and melt (ester interchange) processes could be utilized, as long as they include the initial step of preparing high-purity bisphenol A as described above. Those of ordinary skill in the art understand that the interfacial processes involve the reaction of bisphenol A with a carbonate precursor such as phosgene, in the presence of a base, while the melt processes usually involve the reaction of bisphenol A with diphenyl carbonate. The reactions can be carried out in either a batch mode or a continuous mode. Moreover, related polymers (which fall under the general category of "polycarbonate polymers") can be made in this manner, e.g., polyestercarbonates like those described in U.S. Pat. Nos. 5,274,068 and 4,286,083, incorporated herein by reference.

Many industrial polymer plants are fully integrated, i.e., polycarbonate polymers are made from starting materials that are also manufactured at the plants. In those instances, the overall processes used to prepare polycarbonates are greatly simplified according to this invention, due to the simplification of procedures used in preparing high-purity bisphenol A. Moreover, the final polycarbonate product has all of the desirable characteristics of polycarbonates made by prior art processes, e.g., toughness, clarity, rigidity, and high impact resistance.

EXAMPLES

The following examples are merely illustrative, and should not be construed to be any sort of limitation on the scope of the claimed invention.

Example 1

This example provides a description of the preparation of 2-(4-hydroxyphenyl)-2-propanol, which is then used to prepare bisphenol A in some embodiments of the present invention.

A stirred mixture of methyl lithium (537 ml, 0.564 mol, 1.05M) and diethyl ether (250 ml) was cooled to −78° C. under a blanket of argon gas, using a dry ice/acetone cooling system. A solution of methyl-4-hydroxybenzoate (20 g, 0.131 mol, from Aldrich Chemical Company) in diethyl ether (50 ml) and tetrahydrofuran (50 ml) was added, drop-wise, to the methyl lithium/diethyl ether mixture. The reaction was gradually warmed to room temperature over 12 hours. The reaction was then gently refluxed over a period of 2 hours.

The reaction mixture was then cooled to 0° C., using an ice-water mixture, and quenched with the drop-wise addition of a saturated ammonium chloride solution (250 ml). The mixture was partitioned, and the aqueous layer was washed once with ethyl acetate (200 ml). The organic extracts were combined and washed twice with water (200 ml), and then washed with saturated brine (200 ml). The extracts were then dried over magnesium sulfate, filtered and concentrated, yielding an orange semi-solid. The solid was recrystallized twice from a mixture of diethyl ether/ethyl acetate/hexane (1:1:1 by volume). Two crops were collected and dried, producing 5.5 g (28%) (unoptomized) yield of 2-(4-hydroxyphenyl)-2-propanol. The product was 98.5% pure, as determined by high pressure liquid chromatography (HPLC). Hydrogen proton NMR and UV spectra were consistent with the desired product.

Example 2

This example provides a description of the preparation of p,p'-bisphenol A, using the 2-(4-hydroxyphenyl)-2-propanol which was prepared in Example 1.

A solution of 2-(4-hydroxyphenyl)-2-propanol (74.2 mg, 0.48 mmol) and phenol (1.8801 g, 12.37 mmol) was added to a magnetically-stirred mixture (under nitrogen, at 54° C.) of cysteamine-promoted Amberlite® 131 (518 mg) in phenol. The addition was carried out by using a syringe pump, while the mixture was maintained at 51° C. Upon completion of the addition, the reaction was stirred an additional 1 hour at 60° C. An aliquot was then removed and analyzed by HPLC. There was an 80.4% conversion of the 2-(4-hydroxyphenyl)-2-propanol to p,p'-bisphenol A. The selectivity of p,p'-bisphenol A was found to be 97.8%.

Example 3

This example provides a description of the preparation of p,p'bisphenol A, utilizing a cationic exchange resin catalyst without a promoter, i.e., without co-catalyst.

2-(4-hydroxyphenyl)-2-propanol (100.0 mg, 0.658 mmol; as a solid material) was added in portions to a magnetically-stirred mixture (under nitrogen, at 50° C.) of un-promoted Amberlite® 118 (500 mg) in phenol (5.270 g, 56.1 mmol). The temperature of the solution was maintained at 50° C. during the addition, and during the reaction. After 30 minutes, an aliquot was removed and analyzed by HPLC. The conversion to p,p'-bisphenol A was found to be 81.5%, and the selectivity was determined to be 93.83% p,p'-bisphenol A.

It is expected that some adjustment in reaction conditions such as reaction temperature and phenol content will result in greater selectivity, e.g., greater than about 97% p,p'-bisphenol A.

While preferred embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

All of the patents, articles, and texts mentioned above are incorporated herein by reference.

What is claimed:

1. A method for preparing a polycarbonate polymer, comprising the following steps:

(a) reacting phenol with 2-(4-hydroxyphenyl)-2-propanol in the presence of a catalyst, at a reaction temperature of no greater than about 65° C., to prepare bisphenol A, with a selectivity for the p,p'-isomer of greater than about 97%; and then (b) reacting the p,p'-isomer of bisphenol A with a carbonate precursor, in the presence of a base.

2. The method of claim 1, wherein the carbonate precursor is phosgene.

3. The method of claim 2, wherein step (b) is carried out by an interfacial technique.

4. A method for preparing a polycarbonate polymer, comprising the following steps:

(a) reacting phenol with 2-(4-hydroxyphenyl)-2-propanol in the presence of a catalyst, at a reaction temperature of no greater than about 65° C., to prepare bisphenol A, with a selectivity for the p,p'-isomer of greater than about 97%; and then (b) reacting the p,p'-isomer of bisphenol A prepared in step (a) with diphenyl carbonate in an ester interchange process, to form the polycarbonate.

5. A bisphenol A polycarbonate made by the method of claim 1.

6. An article made from the polycarbonate of claim 5.

7. A bisphenol A polycarbonate made by the method of claim 4.

8. An article made from the polycarbonate of claim 7.

* * * * *